(12) United States Patent
Bender et al.

(10) Patent No.: US 7,348,447 B2
(45) Date of Patent: Mar. 25, 2008

(54) AROMATIC DISILOXANE COMPOSITIONS

(75) Inventors: Timothy P. Bender, Toronto (CA); John F. Graham, Oakville (CA); Yvan Gagnon, Mississauga (CA); Cheng-Kuo Hsiao, Mississauga (CA); Nan-Xing Hu, Oakville (CA); Yu Qi, Oakville (CA)

(73) Assignee: Xerox Corporation, Norwalk, CT (US)

( * ) Notice: Subject to any disclaimer, the term of this patent is extended or adjusted under 35 U.S.C. 154(b) by 234 days.

(21) Appl. No.: 11/246,128

(22) Filed: Oct. 11, 2005

(65) Prior Publication Data

US 2007/0081830 A1   Apr. 12, 2007

(51) Int. Cl.
C07F 7/18 (2006.01)
G03G 15/05 (2006.01)

(52) U.S. Cl. ...................................... 556/479; 399/159
(58) Field of Classification Search ................ 399/159; 556/479; 528/43
See application file for complete search history.

(56) References Cited

U.S. PATENT DOCUMENTS

| | | | | |
|---|---|---|---|---|
| 2,721,873 A | * | 10/1955 | MacKenzie et al. | 556/479 |
| 2,954,390 A | * | 9/1960 | Pike et al. | 556/479 |
| 4,265,990 A | | 5/1981 | Stolka et al. | |
| 4,888,375 A | * | 12/1989 | Greco et al. | 524/262 |
| 5,527,936 A | * | 6/1996 | Dindi et al. | 556/479 |
| 6,048,994 A | * | 4/2000 | Tachikawa et al. | 556/479 |
| 6,165,383 A | * | 12/2000 | Chou | 252/301.16 |
| 6,730,448 B2 | * | 5/2004 | Yoshino et al. | 430/123.42 |
| 7,227,034 B2 | * | 6/2007 | Bender et al. | 562/497 |
| 2003/0232262 A1 | * | 12/2003 | Yamada et al. | 430/58.2 |
| 2004/0082752 A1 | * | 4/2004 | Salamone et al. | 528/43 |
| 2004/0086794 A1 | | 5/2004 | Yamada et al. | |
| 2004/0248032 A1 | * | 12/2004 | Zampini et al. | 430/270.1 |
| 2005/0250925 A1 | * | 11/2005 | Oikawa et al. | 528/25 |
| 2006/0175684 A1 | * | 8/2006 | Oikawa et al. | 257/632 |
| 2007/0112213 A1 | * | 5/2007 | Just et al. | 556/466 |
| 2007/0190325 A1 | * | 8/2007 | Berg-Schultz | 428/402.21 |

FOREIGN PATENT DOCUMENTS

| | | |
|---|---|---|
| JP | A-57-128344 | 8/1982 |
| JP | B2-60-022347 | 6/1985 |
| JP | A-63-065449 | 3/1988 |
| JP | A-04-015659 | 1/1992 |
| JP | B2-05-047104 | 7/1993 |

OTHER PUBLICATIONS

U.S. Appl. No. 10/998,585, filed Nov. 30, 2004, Bender et al.

* cited by examiner

Primary Examiner—Mark Eashoo
Assistant Examiner—Robert Loewe
(74) Attorney, Agent, or Firm—Oliff & Berridge, PLC

(57) ABSTRACT

Processes for preparing aromatic matrix materials by metal hydrosilylation followed by alcholysis are provided. Silicon-containing layers that contain such aromatic matrix materials are also provided, as well as electrophotographic photoreceptors and electrophotographic imaging apparatuses containing such silicon-containing layers.

12 Claims, 4 Drawing Sheets

AROMATIC DISILOXANE COMPOSITIONS

BACKGROUND

This disclosure relates generally to chemical processes for the synthesis of aromatic disiloxane compounds, and to the use of such aromatic disiloxane compounds in producing overcoating layers for electrophotographic imaging members.

In electrophotography, an electrophotographic substrate containing a photoconductive insulating layer on a conductive layer is imaged by first uniformly electrostatically charging a surface of the substrate. The substrate is then exposed to a pattern of activating electromagnetic radiation, such as, for example, light. The light or other electromagnetic radiation selectively dissipates the charge in illuminated areas of the photoconductive insulating layer while leaving behind an electrostatic latent image in non-illuminated areas of the photoconductive insulating layer. This electrostatic latent image is then developed to form a visible image by depositing finely divided electroscopic marking particles on the surface of the photoconductive insulating layer. The resulting visible image is then transferred from the electrophotographic substrate to a necessary member, such as, for example, an intermediate-transfer member or a print substrate, such as paper. This image-developing process can be repeated as many times as necessary with reusable photoconductive insulating layers.

Image-forming apparatus such as copiers, printers and facsimiles, including electrophotographic systems for charging, exposure, development, transfer, etc., using electrophotographic photoreceptors have been widely employed. In such image-forming apparatus, there are ever-increasing demands for improving the speed of the image-forming processes, improving image quality, miniaturizing and prolonging the life of the apparatus, reducing production and running costs, etc. Further, with recent advances in computers and communication technology, digital systems and color-image output systems have been applied also to image-forming apparatus.

Electrophotographic imaging members (i.e. photoreceptors) are well known. Photoreceptors having either a flexible belt or a rigid drum configuration are commonly used in electrophotographic processes. Photoreceptors may comprise a photoconductive layer including a single layer or composite layers. These photoreceptors take many different forms. For example, layered photoresponsive imaging members are known in the art. U.S. Pat. No. 4,265,990 to Stolka et al., which is incorporated herein by reference in its entirety, describes a layered photoreceptor having separate photogenerating and charge-transport layers. The photogenerating layer disclosed in the 990 patent is capable of photogenerating holes and injecting the photogenerated holes into the charge-transport layer. Thus, in the photoreceptors of the 990 patent, the photogenerating material generates electrons and holes when subjected to light.

More advanced photoconductive photoreceptors containing highly specialized component layers are also known. For example, multi-layered photoreceptors may include one or more of a substrate, an undercoating layer, an intermediate layer, an optional hole- or charge-blocking layer, a charge-generating layer (including a photogenerating material in a binder) over an undercoat layer and/or a blocking layer, and a charge-transport layer (including a charge-transport material in a binder). Additional layers, such as one or more overcoat layer or layers, may be included as well.

In view of such a background, improvement in electrophotographic properties and durability, miniaturization, reduction in cost, etc., in photoreceptors have been studied, and photoreceptors using various materials have been proposed.

For example, JP-A-63-065449 (the term "JP-A" as used herein means an "unexamined published Japanese patent application"), which is incorporated herein by reference in its entirety, discloses photoreceptors in which fine silicone particles are added to a photosensitive layer, and also discloses that such addition of the fine silicone particles imparts lubricity to a surface of the photoreceptor.

Further, in forming a photosensitive layer, a method has been proposed in which a charge-transfer substance is dispersed in a binder polymer or a polymer precursor thereof, and then the binder polymer or the polymer precursor thereof is cured. JP-B-05-047104 (the term "JP-B" as used herein means an "examined Japanese patent publication") and JP-B-60-022347, which are incorporated herein by reference in their entirety, disclose photoreceptors using silicone materials as the binder polymers or the polymer precursors thereof.

Furthermore, in order to improve mechanical strength of the photoreceptor, a protective layer is formed on the surface of the photosensitive layer in some cases. Often, a cross-linkable resin is used as a material for the protective layer. However, protective layers formed by cross-linkable resin act as insulating layers, which impair the photoelectric characteristics of the photoreceptor. For this reason, a method of dispersing a fine conductive metal oxide powder, as disclosed in JP-A-57-128344, or a charge-transfer substance, as disclosed in JP-A-04-015659, in the protective layer and a method of reacting a charge-transfer substance having a reactive functional group with a thermoplastic resin to form the protective layer have been proposed. JP-A-57-128344 and JP-A-04-015659 are incorporated herein by reference in their entirety.

The use of silicon-containing compounds in photoreceptor layers, including in photosensitive and protective layers, has been shown to increase the mechanical lifetime of photoreceptors, under charging conditions and scorotron-charging conditions. For example, U.S. Patent Application Publication No. 2004/0086794 to Yamada et al., which is incorporated herein by reference in its entirety, discloses a photoreceptor having improved mechanical strength and stain resistance.

Photoreceptors having low wear rates, such as those described in U.S. Patent Application Publication No. 2004/0086794, also have low refresh rates. Low wear and refresh rates are a primary cause of image-deletion errors, particularly under conditions of high humidity and high temperature. U.S. Pat. No. 6,730,448 to Yoshino et al., which is incorporated herein by reference in its entirety, addresses this issue in its disclosure of photoreceptors having some improvement in image quality, fixing ability, even in an environment of high heat and humidity.

It has been determined that, in photoreceptors, deletion of a developed image is the result of degradation of the top-most surface of the photoreceptor. This deletion occurs when the photoreceptor is exposed to environmental contaminants, such as those typically found around the charging device of a xerographic engine. The image deletion increases under conditions of high heat and/or high humidity.

However, even the above-mentioned conventional photoreceptors are not necessarily sufficient in characteristics and durability, particularly when used in combination with a charger of the contact-charging system (contact charger) or a cleaning apparatus, such as a cleaning blade.

In particular, when the photoreceptor is used in combination with the contact charger and a toner obtained by chemical polymerization (polymerization toner), image quality may be deteriorated if the photoreceptor surface becomes stained with discharge products produced in contact charging or with the polymerization toner remaining after a transfer step. Use of a cleaning blade to remove discharge product or remaining toner from the photoreceptor surface involves friction and abrasion between the surface of the photoreceptor and the cleaning blade. In conventional systems, this high friction and abrasion may damage the surface of the photoreceptor and/or damage the cleaning blade, resulting in premature cleaning blade failure.

Thus, there still remains a need for photoreceptors having high mechanical strength, improved electrophotographic characteristics, improved image-deletion characteristics and reduced friction between protective overcoat layers of the photoreceptor and cleaning blades.

SUMMARY

Silicon-containing layers for photoreceptors, in which the silicon-containing layers have high mechanical strength, improved electrophotographic characteristics and improved image-deletion characteristics even under conditions of high temperature and high humidity are provided.

Separably provided are aromatic matrix materials prepared from aromatic compounds. Aromatic matrix materials prepared by reacting aromatic compounds with silating agents in the presence of metal hydrosilylation catalysts and treating the silated material with alcohol are also provided.

Separably provided are processes for preparing aromatic matrix materials by reacting aromatic compounds with silating agents in the presence of metal hydrosilylation catalysts and treating the silated material with alcohol.

Separably provided are silicon-containing layers for photoreceptors, in which the silicon-containing layers include aromatic matrix materials prepared by reacting aromatic compounds with silating agents in the presence of metal hydrosilylation catalysts and treating the silated material with alcohol.

Separably provided are photoreceptors including silicon-containing layers that include aromatic matrix materials prepared by reacting aromatic compounds with silating agents in the presence of metal hydrosilylation catalysts and treating the silated material with alcohol.

Separably provided are electrophotographic imaging apparatuses including photoreceptors including silicon-containing layers that include aromatic matrix materials prepared by reacting aromatic compounds with silating agents in the presence of metal hydrosilylation catalysts and treating the silated material with alcohol.

These and other features and advantages of various exemplary embodiments of materials, devices, systems and/or methods are described in, or are apparent from, the following detailed description of the various exemplary embodiments of the methods and systems.

DETAILED DESCRIPTION OF EMBODIMENTS

Figure 1:
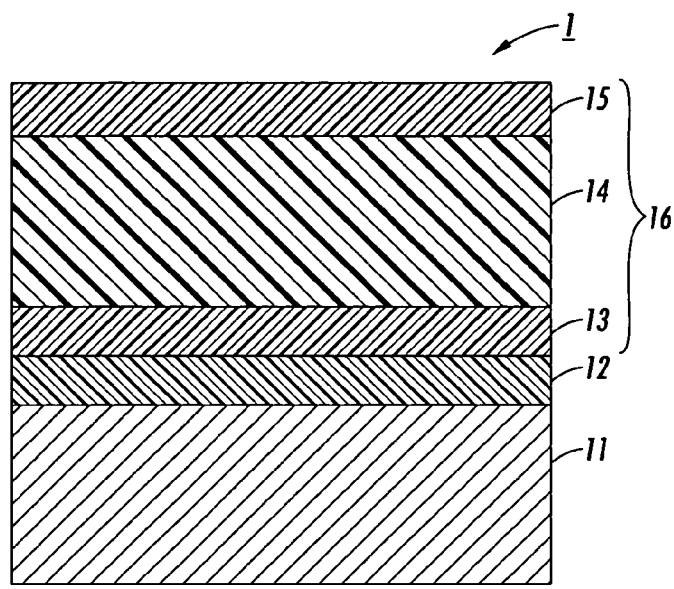
FIG. 1 is a schematic cross-sectional view showing an embodiment of an electrophotographic photoreceptor.

Exemplary embodiments will be described in detail below with reference to drawings in some cases. In the drawings, the same reference numerals and signs are used to designate the same or corresponding parts, and repeated descriptions are avoided.

Photoreceptor

In photoreceptors of embodiments, photosensitive layers may comprise one or more silicon-containing layers, and the silicon-containing layers may further contain resin.

In embodiments, the resin may be a resin soluble in a liquid component in a coating solution used for formation of this layer. Such a liquid-soluble resin may be selected based upon the liquid component employed. For example, if the coating solution contains an alcoholic solvent (such as methanol, ethanol or butanol), a polyvinyl acetal resin such as a polyvinyl butyral resin, a polyvinyl formal resin or a partially acetalized polyvinyl acetal resin in which butyral is partially modified with formal or acetoacetal, a polyamide resin, a cellulose resin such as ethyl cellulose and a phenol resin may be suitably chosen as the alcohol-soluble resins. These resins may be used either alone or as a combination of two or more of them. Of the above-mentioned resins, the polyvinyl acetal resin is used in some embodiments to obtain the benefits of its electric characteristics.

In embodiments, the weight-average molecular weight of the resin soluble in the liquid component may be from about 2,000 to about 1,000,000, and from about 5,000 to about 50,000. When the weight-average molecular weight is less than about 2,000, the effect of enhancing discharge-gas resistance, mechanical strength, scratch resistance, particle dispersibility, etc., tends to become insufficient. However, when the weight-average molecular weight exceeds about 1,000,000, the resin solubility in the coating solution decreases, and the amount of resin added to the coating solution may be limited and poor film formation in the production of the photosensitive layer may result.

Further, the amount of resin soluble in the liquid component may be, in embodiments, from about 0.1 to about 15% by weight, or from about 0.5 to about 10% by weight, based on the total amount of the coating solution. When the amount added is less than about 0.1% by weight, the effect of enhancing discharge-gas resistance, mechanical strength, scratch resistance, particle dispersibility, etc., may become insufficient. However, if the amount of the resin soluble in the liquid component exceeds about 15% by weight, there may be a tendency to form indistinct images when the photoreceptor is used at high temperature and high humidity.

As used herein, a "high-temperature environment" or "high-temperature conditions" refer to an atmosphere in which the temperature is at least about 28° C., such as about 28° C. to about 50° C. or to about 75° C. A "high-humidity environment" or "high-humidity conditions" refer to an atmosphere in which the relative humidity is at least about 75%, such as about 75% to about 90% or about 100%.

Silicon-containing compounds used in embodiments contain at least one silicon atom, but are otherwise not particularly limited. However, a compound containing two or more silicon atoms may be used in embodiments. The use of the compound containing two or more silicon atoms allows both the strength and image quality of the photoreceptor to be achieved at higher levels.

In embodiments, at least one member selected from silicon-containing compounds represented by formulas (2) to (4) and hydrolysates or hydrolytic condensates thereof may be used.

$$W^1(-SiR_{3-a}Q_a)_2 \quad (2)$$

$$W^2(\text{-}D\text{-}SiR_{3-a}Q_a)_b \quad (3)$$

$$SiR_{4-c}Q_c \quad (4)$$

In formulas (2) to (4), $W_1$ represents a divalent organic group, $W^2$ represents an organic group derived from a compound having hole-transport capability, R represents a member selected from the group consisting of a hydrogen atom, an alkyl group and a substituted or unsubstituted aryl group, Q represents a hydrolytic group, D represents a divalent group, a represents an integer of 1 to 3, b represents an integer of 2 to 4, and c represents an integer of 1 to 4.

R in formulas (2) to (4) represents a hydrogen atom, an alkyl group, such as a $C_1$-$C_5$ alkyl group, or a substituted or unsubstituted aryl group, such as a substituted or unsubstituted $C_6$-$C_{15}$ aryl group, as described above.

Further, the hydrolytic group represented by Q in formulas (2) to (4) means a functional group which can form a siloxane bond (O—Si—O) by hydrolysis in the curing reaction of the compound represented by any one of formulas (2) to (4). Non-limiting examples of the hydrolytic groups that may be used in embodiments include a hydroxyl group, an alkoxyl group, a methyl ethyl ketoxime group, a diethylamino group, an acetoxy group, a propenoxy group and a chloro group. In particular embodiments, a group represented by —OR", in which R" represents a $C_1$-$C_{15}$ alkyl group or a trimethylsilyl group, may be used.

In formula (3), the divalent group represented by D may be, in embodiments, a divalent hydrocarbon group represented by —$C_nH_{2n}$—, —$C_nH_{2n-2}$—, —$C_nH_{2n-4}$— (n is an integer of 1 to about 15, such as from 2 to about 10), —$CH_2$—$C_6H_4$— or —$C_6H_4$—$C_6H_4$—, an oxycarbonyl group (—COO—), a thio group (—S—), an oxy group (—O—), an isocyano group (—N=CH—) or a divalent group in which two or more such divalent groups are combined. The divalent group may have a substituent group such as an alkyl group, a phenyl group, an alkoxl group or an amino group on its side chain. In embodiments in which D is one of the above-mentioned divalent groups, proper flexibility may be imparted to an organic silicate skeleton, thereby tending to improve the strength of the layer.

Non-limiting examples of compounds representable by formula (2) include disiloxane compounds, such as those shown in Table 1. As used herein, "Me" indicates a methyl (—$CH_3$) group; "OMe" indicates a methoxy (—$OCH_3$) group; "Et" indicates an ethyl (—$CH_2CH_3$) group; "OEt" indicates an ethoxy (—$OCH_2CH_3$) group; "i-Pr" indicates an isopropyl (—$CH(CH_3)_2$) group; "O-i-Pr" indicates an isopropoxy (—$OCH(CH_3)_2$) group.

TABLE 1

| No. | Structural Formula |
|---|---|
| III-1 | (MeO)$_3$Si—(CH$_2$)$_2$—Si(OMe)$_3$ |
| III-2 | (MeO)$_2$Me—(CH$_2$)$_2$—SiMe(OMe)$_2$ |
| III-3 | (MeO)$_2$MeSi—(CH$_2$)$_6$—SiMe(OMe)$_2$ |
| III-4 | MeO)$_3$Si—(CH$_2$)$_6$—Si(OMe)$_3$ |
| III-5 | (EtO)$_3$Si—(CH$_2$)$_6$—Si(OEt)$_3$ |
| III-6 | (MeO)$_2$MeSi—(CH$_2$)$_{10}$—SiMe(OMe)$_2$ |
| III-7 | (MeO)$_3$Si—(CH$_2$)$_3$—NH—(CH$_2$)$_3$—Si(OMe)$_3$ |
| III-8 | (MeO)$_3$Si—(CH$_2$)$_3$—NH—(CH$_2$)$_2$—NH—(CH$_2$)$_3$—Si(OMe)$_3$ |
| III-9 |  |
| III-10 | 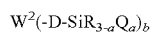 |
| III-11 |  |
| III-12 | |
| III-13 | |

TABLE 1-continued

No. Structural Formula

III-14

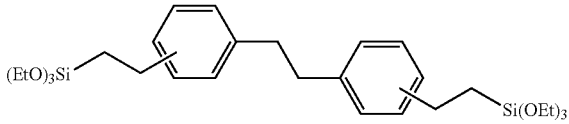

III-15  (MeO)$_3$SiC$_3$H$_6$—O—CH$_2$CH{—O—C$_3$H$_6$Si(OMe)$_3$}—CH$_2${—O—C$_3$H$_6$Si(OMe)$_3$}
III-16  (MeO)$_3$SiC$_2$H$_4$—SiMe$_2$—O—SiMe$_2$—O—SiMe$_2$—C$_2$H$_4$Si(OMe)$_3$

Further, in formula (3), W$^2$ is not particularly limited. However, in particular embodiments, W$^2$ may be an organic group represented by formula (6):

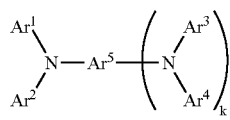

(6)

wherein Ar$^1$, Ar$^2$, Ar$^3$ and Ar$^4$, which may be the same or different, each represents a substituted or unsubstituted aryl group, Ar$^5$ represents a substituted or unsubstituted aryl or arylene group, k represents 0 or 1, and at least one of Ar$^1$ to Ar$^5$ has a bonding hand to connect with -D-SiR$_{3-a}$Q$_a$ in formula (3).

Figure 4:
FIG. 4 sets forth exemplary siloxane-containing arylamine compounds.

Combinations of Ar$^1$, Ar$^2$, Ar$^3$, Ar$^4$, Ar$^5$ and integer k in formula (6) and a group represented by -D-SiR$_{3-a}$Q$_a$ in formula (3) include the particular exemplary embodiments shown in FIG. 4; additional exemplary embodiments can be found in U.S. Patent Application Publication No. 2004/0086794, U.S. Pat. No. 6,730,448 and in U.S. patent application Ser. No. 10/998,585, entitled "Silicon-Containing Layers for Electrophotographic Photoreceptors and Methods for Making the Same," the entire disclosures of which are incorporated herein by reference. As used in FIG. 4, S represents -D—SiR$_{3-a}$Q$_a$ linked to Ar$^1$ to Ar$^5$.

Further, in embodiments, the silicon compounds represented by formula (4) may include silane coupling agents such as monofunctional alkoxysilanes (c=1) such as trimethylmethoxysilane; bifunctional alkoxysilanes (c=2) such as dimethyldimethoxysilane, diphenyldimethoxysilane or methylphenyldimethoxysilane; trifunctional alkoxysilanes (c=3) such as methyltrimethoxysilane, methyltriethoxy-silane, ethyltrimethoxysilane, methyltrimethoxyethoxysilane, vinyltrimethoxysilane, vinyltriethoxysilane, phenyltrimethoxysilane, γ-glycidoxypropylmethyldiethoxysilane, γ-glycidoxypropyltrimethoxysilane, γ-glycidoxypropyltriethoxysilane, γ-aminopropyl-triethoxysilane, γ-aminopropyltrimethoxysilane, γ-aminopropylmethyldimethoxy-silane, N-β-(aminoethyl)-γ-aminopropyltriethoxysilane, (tridecafluoro-1,1,2,2-tetrahydrooctyl)triethoxysilane, (3,3,3-trifluoropropyl)trimethoxysilane, 3-(heptafluoroisopropoxy)propyltriethoxysilane, 1H,1H,2H,2H-perfluoroalkyl-triethoxysilane, 1H,1H,2H,2H-perfluorodecyltriethoxysilane or 1H,1H,2H,2H-perfluorooctyltriethoxysilane; and tetrafunctional alkoxysilanes (c=4) such as tetramethoxysilane or tetraethoxysilane.

In order to improve the strength of the photosensitive layer, trifunctional and tetrafunctional alkoxysilanes may be used in embodiments, and in order to improve the flexibility and film-forming properties, monofunctional and bifunctional alkoxysilanes may be used in embodiments.

Silicone hard coating agents containing these coupling agents can also be used in embodiments. Commercially available hard-coating agents include KP-85, X-40-9740 and X-40-2239 (available from Shinetsu Silicone Co., Ltd.), and AY42-440, AY42-441 and AY49-208 (available from Toray Dow Corning Co., Ltd.).

In embodiments, the silicon-containing layer may contain one or more of the silicon-containing compounds represented by formulas (2) to (4). Further, the compounds represented by formulas (2) to (4) may include monofunctional compounds (in which a or c is 1), bifunctional compounds (in which a or c is 2), trifunctional compounds (in which a or c is 3) and/or tetrafunctional compounds (in which a or c is 4). However, in particular embodiments, the number of silicon atoms derived from the silicon-containing compounds represented by formulas (2) to (4) in the silicon-containing layer satisfies equation (26):

$$N_{a=3} + N_{c\geq 3})/N_{total} \leq 0.5 \quad (26)$$

wherein $N_{a=3}$ represents the number of silicon atoms derived from —SiR$_{3-a}$Q$_a$ of the silicon-containing compound represented by formula (2) or (3), in which a is 3; $N_{c\geq 3}$ represents the number of silicon atoms derived from the silicon-containing compound represented by formula (4) in which c is 3 or 4; and $N_{total}$ represents the total of the number of silicon atoms derived from —SiR$_{3-a}$Q$_a$ of the silicon compound represented by formula (2) or (3) and the number of silicon atoms derived from the silicon-containing compound represented by formula (4). That is, the ratio of silicon-containing compounds contained is set so that the number of silicon atoms derived from the trifunctional compound or the tetrafunctional compound becomes 0.5 or less based on the number of silicon atoms derived from the silicon-containing compounds represented by formulas (2) to (4) (in the case of the compound represented by formula (2) or (3), the silicon atoms are limited to ones derived from —SiR$_{3-a}$Q$_a$, and the same applies hereinafter). When the value of the left side of equation (26) exceeds 0.5, indistinct images may occur at high temperature and high humidity. When the value of the left side of equation (26) is decreased, a decrease in strength may also result. However, the use of a silicon-containing compound having two or more silicon atoms in its molecule can improve the strength.

In order to further improve the stain-adhesion resistance and lubricity of embodiments of photoreceptors, various fine particles can also be added to the silicon-containing layer. Non-limiting examples of the fine particles include fine particles containing silicon, such as fine particles containing silicon as a constituent element, and specifically include colloidal silica and fine silicone particles. Fine particles may be used either alone or as a combination of two or more of such fine particles.

Colloidal silica used in embodiments as the fine particles containing silicon may be selected from acidic or alkaline aqueous dispersions of fine particles having an average particle size of about 1 to about 100 nm, or about 10 to about 30 nm, and dispersions of fine particles in organic solvents, such as an alcohol, a ketone or an ester. In general, commercially available particles may be used. There is no particular limitation on the solid content of colloidal silica in a top surface layer of the photoreceptor of embodiments. However, in embodiments, colloidal silica is used within the range of from about 1 to about 50% by weight, such as in a range of from about 5 to about 30% by weight, based on the total solid content of the top-surface layer, in terms of film-forming properties, electric characteristics and strength.

Fine silicone particles that may be used as fine particles containing silicon in embodiments may be selected from silicone resin particles, silicone rubber particles and silica particles surface-treated with silicone. Such particles may be spherical and may have an average particle size in a range of from about 1 to about 500 nm, such as from about 10 to about 100 nm. In general, commercially available particles may be used in embodiments.

In embodiments, the fine silicone particles are small-sized particles that are chemically inactive and excellent in dispersibility in a resin, and further are low in content as may be necessary for obtaining sufficient characteristics. Accordingly, the surface properties of exemplary photoreceptors can be improved without inhibition of the cross-linking reaction. That is, fine silicone particles improve the lubricity and water repellency of photoreceptor surfaces where incorporated into strong cross-linked structures, which may then be able to maintain good wear resistance and stain-adhesion resistance for a long period of time. The content of the fine silicone particles in the silicon-containing layer of embodiments may be within the range of from about 0.1 to about 20% by weight, such as from about 0.5 to about 10% by weight, based on the total solid content of the silicon-containing layer.

Other fine particles that may be used in embodiments include fine fluorine-based particles, such as ethylene tetrafluoride, ethylene trifluoride, propylene hexafluoride, vinyl fluoride and vinylidene fluoride, and semiconductive metal oxides such as $ZnO$—$Al_2O_3$, $SnO_2$—$Sb_2O_3$, $In_2O_3$—$SnO_2$, $ZnO$—$TiO_2$, $MgO$—$Al_2O_3$, $FeO$—$TiO_2$, $TiO_2$, $SnO_2$, $In_2O_3$, $ZnO$ and $MgO$.

In conventional photoreceptors, when such fine particles are contained in the photosensitive layer, the compatibility of the fine particles with a charge-transfer substance or a binding resin may become insufficient, which causes layer separation in the photosensitive layer, and thus forms an opaque film. As a result, the electric characteristics have deteriorated in some cases. In contrast, the silicon compound-containing layer of embodiments, such as for example a charge-transfer layer, may contain the resin soluble in the liquid component in the coating solution used for formation of this layer and the silicon compound, thereby improving the dispersibility of the fine particles in the silicon compound-containing layer. Accordingly, the pot life of the coating solution can be sufficiently prolonged, and it becomes possible to prevent deterioration of the electric characteristics.

Further, an additive such as a plasticizer, a surface modifier, an antioxidant, or an agent for preventing deterioration by light may also be included in the silicon compound-containing layer of embodiments. Non-limiting examples of plasticizers that may be used in embodiments include, for example, biphenyl, biphenyl chloride, terphenyl, dibutyl phthalate, diethylene glycol phthalate, dioctyl phthalate, triphenylphosphoric acid, methylnaphthalene, benzophenone, chlorinated paraffin, polypropylene, polystyrene and various fluorohydrocarbons.

The antioxidants may include an antioxidant having a hindered-phenol, hindered-amine, thioether or phosphite partial structure. Suitable antioxidants include antioxidants having hindered-phenol, hindered-amine, thioether or phosphite partial structures, which may improve potential stability and image quality in environmental variation. Suitable hindered-phenol antioxidants for use in embodiments include butylated hydroxytoluenes (such as 2,6-di-tert-butyl-4-methylphenol or BHT), SUMILIZER BHT-R, SUMILIZER MDP-S, SUMILIZER BBM-S, SUMILIZER WX-R, SUMILIZER NW, SUMILIZER BP-76, SUMILIZER BP-101, SUMILIZER GA-80, SUMILIZER GM and SUMILIZER GS (available from Sumitomo Chemical Co., Ltd.); IRGANOX 1010, IRGANOX 1035, IRGANOX 1076, IRGANOX 1098, IRGANOX 1135, IRGANOX 1141, IRGANOX 1222, IRGANOX 1330, IRGANOX 1425WLj, IRGANOX 1520Lj, IRGANOX 245, IRGANOX 259, IRGANOX 3114, IRGANOX 3790, IRGANOX 5057 and IRGANOX 565 (available from Ciba Specialty Chemicals); and ADECASTAB AO-20, ADECASTAB AO-30, ADECASTAB AO-40, ADECASTAB AO-50, ADECASTAB AO-60, ADECASTAB AO-70, ADECASTAB AO-80 and ADECASTAB AO-330i (available from Asahi Denka Co., Ltd.). Suitable hindered-amine antioxidants that may be used in embodiments include SANOL LS2626, SANOL LS765, SANOL LS770, SANOL LS744, TINUVIN 144, TINUVIN 622LD, MARK LA57, MARK LA67, MARK LA62, MARK LA68, MARK LA63 and SUMILIZER TPS; and suitable phosphite antioxidants that may be used in embodiments include MARK 2112, MARK PEP.8, MARK PEP.24G, MARK PEP.36, MARK 329K and MARK HP.10. In particular embodiments, the antioxidant is one or more antioxidant chosen from hindered-phenol and hindered-amine antioxidants.

A siloxane-containing antioxidant may also be incorporated into the silicon-containing layer of embodiments. In certain embodiments, the siloxane-containing antioxidant may be wholly or at least partially located in the siloxane region of the silicon-containing layer. The siloxane-containing antioxidants may include any siloxane-containing antioxidant having a hindered-phenol, hindered-amine, thioether or phosphite partial structure. Use of siloxane-containing antioxidants having a hindered-phenol, hindered-amine, thioether or phosphite partial structure, as described herein, has been found to drastically improve image-deletion characteristics even in long-term cycling under conditions of high humidity and high temperature. Suitable siloxane-containing antioxidants that may be used in accordance with embodiments can be found in U.S. patent application Ser. No. 10/998,585.

There is no particular limitation on the thickness of the silicon-containing layer, however, in embodiments, the silicon-containing layer may be in a range from about 2 to about 5 µm in thickness, such as about 2.7 to about 3.2 µm in thickness.

The photoreceptor of embodiments may be either a function-separation-type photoreceptor, in which a layer containing a charge-generation substance (charge-generation layer) and a layer containing a charge-transfer substance (charge-transfer layer) are separately provided, or a monolayer-type photoreceptor, in which both the charge-generation layer and the charge-transfer layer are contained in the same layer, as long as the photoreceptor of the particular embodiment has the photosensitive layer provided with the above-mentioned silicon compound-containing layer. The photoreceptor of embodiments will be described in greater detail below, taking the function-separation-type photoreceptor as an example.

FIG. 1 is a cross-sectional view schematically showing an embodiment of a photoreceptor. Photoreceptor 1 shown in FIG. 1 is a function-separation-type photoreceptor in which charge-generation layer 13 and charge-transfer layer 14 are separately provided. That is, underlayer 12, charge-generation layer 13, charge-transfer layer 14 and protective layer 15 are laminated onto conductive support 11 to form photosensitive layer 16. Protective layer 15 contains a resin soluble in the liquid component contained in the coating solution used for formation of this layer and the silicon compound.

Conductive support 11 may include, for example, a metal plate, a metal drum or a metal belt using a metal, such as aluminum, copper, zinc, stainless steel, chromium, nickel, molybdenum, vanadium, indium, gold, platinum or an alloy thereof; and paper or a plastic film or belt coated, deposited or laminated with a conductive polymer, a conductive compound such as indium oxide, or a metal such as aluminum, palladium, gold, or an alloy thereof. Further, surface treatment (such as anodic oxidation coating, hot water oxidation, chemical treatment, or coloring) or diffused reflection treatment (such as graining) can also be applied to a surface of support 11.

Binding resins used in underlayer 12 of embodiments may include but are not limited to, one or more polyamide resins, vinyl chloride resins, vinyl acetate resins, phenol resins, polyurethane resins, melamine resins, benzoguanamine resins, polyimide resins, polyethylene resins, polypropylene resins, polycarbonate resins, acrylic resins, methacrylic resins, vinylidene chloride resins, polyvinyl acetal resins, vinyl chloride-vinyl acetate copolymers, polyvinyl alcohol resins, water-soluble polyester resins, nitrocelluloses, caseins, gelatins, polyglutamic acids, starches, starch acetates, amino starches, polyacrylic acids, polyacrylamides, zirconium chelate compounds, titanyl chelate compounds, titanyl alkoxide compounds, organic titanyl compounds, silane coupling agents and mixtures thereof. Further, fine particles of titanium oxide, aluminum oxide, silicon oxide, zirconium oxide, barium titanate, a silicone resin or the like may be added to the above-mentioned binding resin in embodiments.

As a coating method in forming the underlayer of embodiments, any ordinary method, such as blade coating, Mayer bar coating, spray coating, dip coating, bead coating, air knife coating or curtain coating may be employed. The thickness of the underlayer may be from about 0.01 to about 40 μm in embodiments.

Non-limiting examples of charge-generation substances that may be contained in charge-generation layer 13 of embodiments include, but are not limited to, various organic pigments and organic dyes; such as azo pigments, quinoline pigments, perylene pigments, indigo pigments, thioindigo pigments, bisbenzimidazole pigments, phthalocyanine pigments, quinacridone pigments, quinoline pigments, lake pigments, azo lake pigments, anthraquinone pigments, oxazine pigments, dioxazine pigments, triphenylmethane pigments, azulenium dyes, squalium dyes, pyrylium dyes, triallylmethane dyes, xanthene dyes, thiazine dyes and cyanine dyes; and inorganic materials such as amorphous silicon, amorphous selenium, tellurium, selenium-tellurium alloys, cadmium sulfide, antimony sulfide, zinc oxide and zinc sulfide. In embodiments, cyclo-condensed aromatic pigments, perylene pigments and azo pigments may be used to impart sensitivity, electric stability and photochemical stability against irradiated light. These charge-generation substances may be used either alone or as a combination of two or more.

In embodiments, charge-generation layer 13 may be formed by vacuum deposition of the charge-generation substance or application of a coating solution in which the charge-generation substance is dispersed in an organic solvent containing a binding resin. The binding resins used in the charge-generation layer of embodiments include polyvinyl acetal resins such as polyvinyl butyral resins, polyvinyl formal resins or partially acetalized polyvinyl acetal resins in which butyral is partially modified with formal or acetoacetal, polyamide resins, polyester resins, modified ether type polyester resins, polycarbonate resins, acrylic resins, polyvinyl chloride resins, polyvinylidene chlorides, polystyrene resins, polyvinyl acetate resins, vinyl chloride-vinyl acetate copolymers, silicone resins, phenol resins, phenoxy resins, melamine resins, benzoguanamine resins, urea resins, polyurethane resins, poly-N-vinylcarbazole resins, polyvinylanthracene resins, polyvinylpyrene resins and mixtures thereof. In embodiments in which one or more of polyvinyl acetal resins, vinyl chloride-vinyl acetate copolymers, phenoxy resins or modified ether type polyester resins are used, the dispersibility of the charge-generation substance may be improved to cause no occurrence of coagulation of the charge-generation substance, and a coating solution that is stable for a long period of time may be obtained. The use of such a coating solution in embodiments makes it possible to form a uniform coating easily and surely. As a result, the electric characteristics may be improved, and image defects may be prevented. Further, the compounding ratio of the charge-generation substance to the binding resin may be, in embodiments, within the range of from about 5:1 to about 1:2 by volume ratio.

Further, the solvents used in preparing the coating solution of embodiments may include organic solvents such as methanol, ethanol, n-propanol, n-butanol, benzyl alcohol, methyl cellosolve, ethyl cellosolve, acetone, methyl ethyl ketone, cyclohexanone, chlorobenzene, methyl acetate, n-butyl acetate, dioxane, tetrahydrofuran, methylene chloride, chloroform and mixtures thereof.

Methods for applying the coating solution in embodiments include the coating methods described above with reference to the underlayer. The thickness of charge-generation layer 13 thus formed may be from about 0.01 to about 5 μm, such as from about 0.1 to about 2 μm. When the thickness of charge-generation layer 13 is less than about 0.01 μm, uniform layer formation may be difficult. On the other hand, when the thickness exceeds about 5 μm, the electrophotographic characteristics may significantly deteriorate.

Further, a stabilizer such as an antioxidant or an inactivating agent may also be added to charge-generation layer 13 in embodiments. Non-limiting examples of antioxidants that may be used include but are not limited to antioxidants such as phenolic, sulfur, phosphorus and amine compounds, as well as the antioxidant compounds described above. Inactivating agents that may be used in embodiments may include bis(dithiobenzyl)nickel and nickel di-n-butylthiocarbamate.

In embodiments, charge-transfer layer 14 can be formed by applying a coating solution containing the charge-transfer substance and a binding resin, and further fine particles, an additive, etc., as described above.

Low molecular-weight charge-transfer substances that may be used in embodiments may include, for example, pyrene, carbazole, hydrazone, oxazole, oxadiazole, pyrazoline, arylamine, arylmethane, benzidine, thiazole, stilbene and butadiene compounds. In embodiments, high molecular-weight charge-transfer substances may be used and include, for example, poly-N-vinylcarbazoles, poly-N-vinylcarbazole halides, polyvinyl pyrenes, polyvinylanthracenes, polyvinylacridines, pyrene-formaldehyde resins, ethylcarbazole-formaldehyde resins, triphenylmethane polymers and polysilanes. Triphenylamine compounds, triphenylmethane compounds and benzidine compounds may be used in embodiments to promote mobility, stability and transparency to light. Further, silicon compound represented by formula (3) may also be used as charge-transfer substances in particular embodiments.

Other exemplary charge-transfer molecules include, but are not limited to, the various compounds identified above as the organic group $W^2$, which have hole-transport capability. In particular embodiments, the charge-transfer molecule is the arylamine of formula (7):

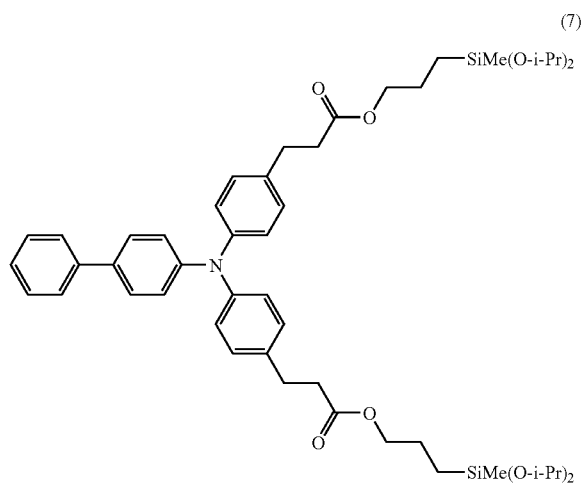

(7)

As binding resins in embodiments, high molecular-weight polymers that can form an electrical insulating film may be used. For example, when polyvinyl acetal resins, polyamide resins, cellulose resins, phenol resins, etc., which are soluble in alcoholic solvents, are used, binding resins used together with these resins include polycarbonates, polyesters, methacrylic resins, acrylic resins, polyvinyl chlorides, polyvinylidene chlorides, polystyrenes, polyvinyl acetates, styrene-butadiene copolymers, vinylidene chloride-acrylonitrile copolymers, vinyl chloride-vinyl acetate copolymers, vinyl chloride-vinyl acetate-maleic anhydride copolymers, silicone resins, silicone-alkyd resins, phenol-formaldehyde resins, styrene-alkyd resins, poly-N-vinylcarbazoles, polyvinyl butyrals, polyvinyl formals, polysulfones, casein, gelatin, polyvinyl alcohols, phenol resins, polyamides, carboxymethyl celluloses, vinylidene chloride-based polymer latexes and polyurethanes. Of the above-mentioned high molecular-weight polymers, polycarbonates, polyesters, methacrylic resins and acrylic resins have excellent compatibility with the charge-transfer substance, solubility and strength.

Charge-transfer layer 14 of embodiments may further contain an additive such as a plasticizer, a surface modifier, an antioxidant or an agent for preventing deterioration by light.

The thickness of charge-transfer layer 14 may be, in embodiments, from about 5 to about 50 μm, such as from about 10 to about 40 μm. When the thickness of the charge-transfer layer is less than about 5 μm, charging becomes difficult. However, thicknesses exceeding about 50 μm result significant deterioration of the electrophotographic characteristics.

Protective layer 15 may contain, in embodiments, resins soluble in liquid components in coating solution used for formation of protective layers and silicon compounds as described above. Protective layer 15 may further contain a lubricant or fine particles of silicone oils or fluorine materials, which can also improve lubricity and strength. Non-limiting examples of the lubricants that may be used in embodiments include the above-mentioned fluorine-based silane coupling agents. Fine particles to be dispersed in protective layer 15 of embodiments may include fine particles comprising resins obtained by copolymerizing fluororesins with hydroxyl group-containing monomers, as described in Proceedings of Lectures in the Eighth Polymer Material Forum, page 89, and semiconductive metal oxides, as well as the above-mentioned fine silicone particles and fine fluorine-based particles. The thickness of the protective layer may be, in embodiments, from about 0.1 to about 10 μm, such as from about 0.5 to about 7 μm.

Photoreceptors prepared using conventional silicon-overcoat technology suffer from initial torque problems associated with high friction between the overcoat layer and the cleaning blade, which may result in premature cleaning-blade failure.

However, in embodiments disclosed herein, the silicon-overcoat layer or protective layer may comprise a siloxane-containing hole-transport molecule. The siloxane-containing hole-transport molecule may be chemically cross-linked with a siloxane-containing binder material; this cross-linking reaction forms a hard siloxane-containing overcoat layer.

The siloxane-containing binder materials of embodiments may be chosen from aromatic binder materials that contain silicon. When siloxane-containing aromatic binder materials are incorporated into the silicon overcoat layer, friction between the photoreceptor and cleaning blades may be greatly reduced. Such an overcoat layer can increase the photoreceptor mechanical lifetime to up to 10 times the lifetime of conventional photoreceptors, and the mechanical lifetime may be further increased under scorotron-charging conditions. The increased mechanical lifetime, the low photoreceptor surface wear rate, may cause a decrease in the refresh rate of the photoreceptor surface as well.

Suitable siloxane-containing aromatic binder materials include, for example, monosiloxane and disiloxane compounds derived from aromatic binder materials, such as vinylbenzene, $C_1$-$C_6$ alkyl vinylbenzenes and divinylbenzenes, and mixtures thereof. In particular, suitable aromatic binder materials may be prepared by catalytic hydrosilylation, in an organic solvent such as for example toluene, of divinylbenzenes, followed by treatment with alcohol. Because suitable divinylbenzenes may include a mixture of monovinylbenzenes, divinylbenzenes and isomers of divinylbenzenes, a mixture of monosiloxane and disiloxane compounds may be formed upon hydrosilylation. For example, an 80% technical-grade divinylbenzene composition (available from Aldrich Chemical Company, Milwaukee, Wis. for example) includes 24.70% p-divinylbenzene, 55.40% m-divinylbenzene, 18.80% ethylvinylbenzenes and 0.05% of other materials; and a 55% technical-grade divinylbenzene composition (available from Aldrich Chemical Company, Milwaukee, Wis. for example) includes 55% divinylbenzenes, 44% ethylvinylbenzenes and 1% of other materials.

Suitable silating agents include, for example, optionally halogenated alkyl silane and alkoxysilane compounds. In particular, suitable silating agents include, for example, $C_1$-$C_6$ alkyl dihalosilanes, such as methyldichlorosilane; and di($C_1$-$C_6$ alkyl) halosilanes, such as dimethylchlorosilane; $C_1$-$C_6$ alkyl dialkoxysilanes, such as methyldimethoxysilane; and di($C_1$-$C_6$ alkyl) alkoxysilanes, such as dimethylmethoxysilane.

Suitable hydrosilylation catalysts include, for example, transition metal hydrosilylation catalysts. For example, platinum hydrosilylation catalysts, such as the Karstedt catalyst, $Pt_2$(divinyltetramethyldisiloxane)$_3$, may be used in embodiments. Although embodiments are described herein with reference to the Karstedt catalyst, other known or later developed or discovered catalysts that effect hydrosilylation reactions may also be used in embodiments. It is noted that reactions using the Karstedt catalyst are known to have an induction period, after which these reactions can be extremely exothermic. Thus, it is desirable to use an oversized reaction flask with a very high cooling capacity and large head space for such reactions.

Following hydrosilylation, the products are treated with alcohol in the presence of tertiary amine compounds or other hydrogen-halide scavenger materials or compounds. Alcohol treatment may be accomplished using any suitable alcohol, including, for example, $C_1$-$C_{20}$ alcohols, which may be branched, cyclic or linear. Amine compounds act as scavenger materials for by-products such as hydrogen halides, such as hydrogen chloride. Suitable amine compounds include, for example, tertiary amine compounds, such as triethylamine.

For example, in particular exemplary embodiments, an aromatic binder material is prepared by reacting a mixture of monovinylbenzenes, divinylbenzenes and isomers of divinylbenzenes with methyldichlorosilane in the presence of the Karstedt catalyst, followed by treating the reaction mixture with, for example, a solution of triethylamine in methanol, as shown below.

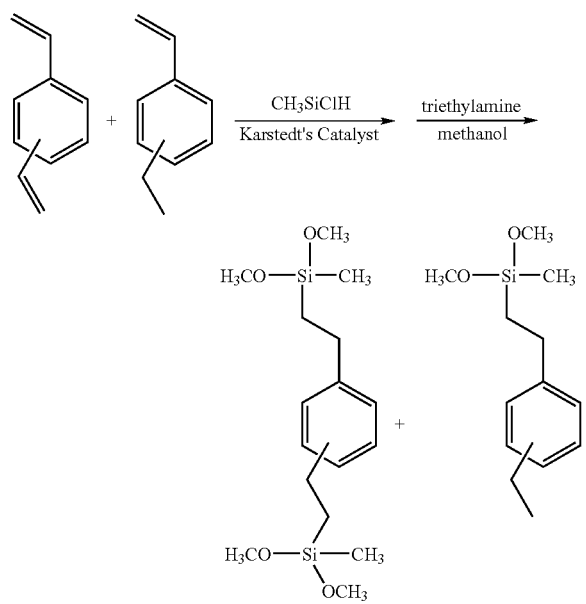

The aromatic binder material includes ten reaction products, including the monosilane and disilane products of both Markovnikov (M) and anti-Markovnikov (A) addition to m-divinylbenzene, p-divinylbenzene and ethylvinylbenzene. These products may be separated from the reaction mixture by any suitable method, such as filtration of insoluble triethylamine hydrochloride and concentration by rotary evaporation. Because the reaction conditions of embodiments may use an excess amount of methyldichlorosilane, residual methyldimethoxysilane may be present. In addition, similar amounts of hydrogen transfer may occur, producing saturated hydrocarbon materials having boiling points lower than the boiling points of the desired siloxane materials. Other, higher boiling siloxane compounds may also be present if water is not meticulously removed from the reaction vessel. Vacuum distillation may be used to isolate the desired mixture from the lower boiling materials and the higher boiling siloxane compounds. However, after separation from lower boiling point materials and the higher boiling siloxane compounds, the monosilane and disilane products may be incorporated into the siloxane-containing layer of embodiments individually or as a mixture of two or more such reaction products. That is, it is not necessary to separate the monosilane and disilane reaction products into individual components; all of the reaction products may be incorporated together into the siloxane-containing layer of embodiments.

The photoreceptor of embodiments should not be construed as being limited to the above-mentioned constitution. For example, the photoreceptor shown in FIG. 1 is provided with protective layer 15. However, when charge-transfer layer 14 contains the resin soluble in the liquid component in the coating solution used for formation of this layer and the silicon compound, charge-transfer layer 14 may be used as a top surface layer (a layer on the side farthest apart from support 11) without using protective layer 15. In some embodiments, the charge-transfer substance contained in charge-transfer layer 14 may be soluble in the liquid component in the coating solution used for formation of charge-transfer layer 14.

Image-Forming Apparatus and Process Cartridge

Figure 2:
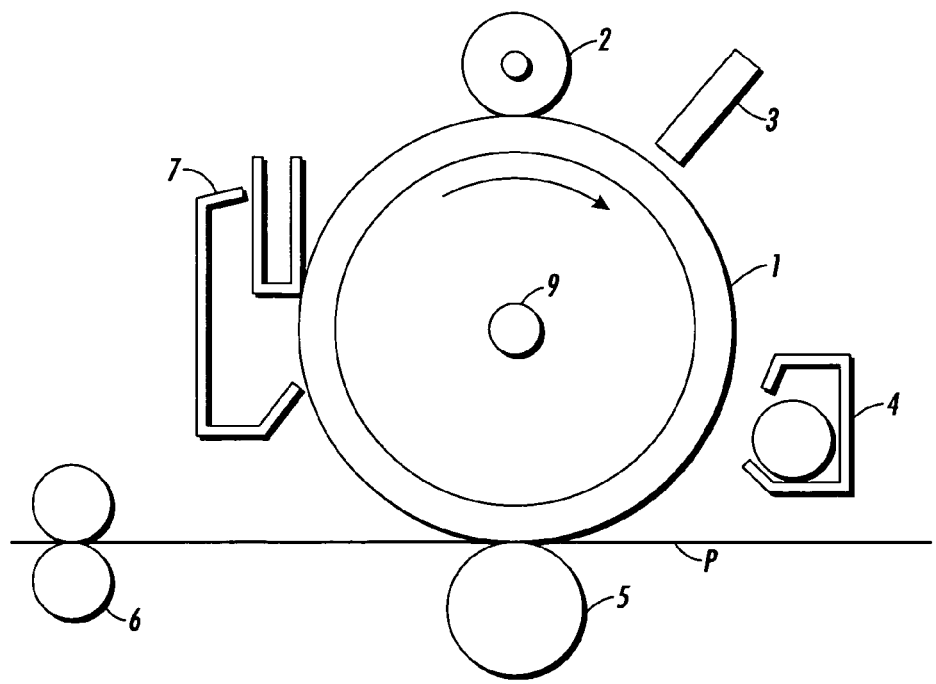
FIG. 2 is a schematic view showing an embodiment of an image-forming apparatus.

FIG. 2 is a schematic view showing an embodiment of an image-forming apparatus. In the apparatus shown in FIG. 2, photoreceptor 1 constituted as shown in FIG. 1 is supported by support 9, and rotatable at a specified rotational speed in the direction indicated by the arrow, centered on support 9. Contact-charging device 2, exposure device 3, developing device 4, transfer device 5 and cleaning unit 7 are arranged in this order along the rotational direction of photoreceptor 1. Further, this exemplary apparatus is equipped with image-fixing device 6, and medium P to which a toner image is to be transferred is conveyed to image-fixing device 6 through transfer device 5.

Contact-charging device 2 has a roller-shaped contact-charging member. The contact-charging member is arranged so that it comes into contact with a surface of photoreceptor 1, and a voltage is applied, thereby being able to give a specified potential to the surface of photoreceptor 1. In embodiments, a contact-charging member may be formed from a metal, such as aluminum, iron or copper; a conductive polymer material, such as a polyacetylene, a polypyrole or a polythiophene; or a dispersion of fine particles of carbon black, copper iodide, silver iodide, zinc sulfide, silicon carbide, a metal oxide or the like, in an elastomer material, such as polyurethane rubber, silicone rubber, epichlorohydrin rubber, ethylene-propylene rubber, acrylic rubber, fluororubber, styrene-butadiene rubber or butadiene rubber. Non-limiting examples of metal oxides that may be used in embodiments include $ZnO$, $SnO_2$, $TiO_2$, $In_2O_3$, $MoO_3$ and complex oxides thereof. Further, a perchlorate may be added to the elastomer material to impart conductivity.

Further, a covering layer may also be provided on a surface of the contact-charging member of embodiments. Non-limiting examples of materials that may be used in embodiments for forming a covering layer include N-alkoxy-methylated nylon, cellulose resins, vinylpyridine resins, phenol resins, polyurethanes, polyvinyl butyrals, melamines and mixtures thereof. Furthermore, resin emulsion materials such as acrylic resin emulsions, polyester resin emulsions or polyurethanes, may be used. In order to further adjust resistivity, conductive-agent particles may be dispersed in these resins, and in order to prevent deterioration, an antioxidant can also be added thereto. Further, in order to improve film-forming properties in forming the covering layer, a leveling agent or a surfactant may be added to the emulsion resin in embodiments.

The resistance of the contact-charging member of embodiments may be in a range of from about $10^0$ to about $10^{14}$ Ω-cm, such as from about $10^2$ to about $10^{12}$ Ω-cm. When a voltage is applied to this contact-charging member, either a DC (direct current) voltage or an AC (alternating current) voltage can be used as the applied voltage. Further, a superimposed voltage of a DC voltage and an AC voltage can also be used.

In the exemplary apparatus shown in FIG. 2, contact-charging member of contact-charging device 2 is in the shape of a roller. However, such a contact-charging member may be in the shape of a blade, a belt, a brush or the like.

Further, in embodiments an optical device that can perform desired imagewise exposure to a surface of photoreceptor 1 with a light source such as a semiconductor laser, an LED (light emitting diode) or a liquid crystal shutter, may be used as exposure device 3.

Furthermore, a known developing device using a normal or reversal developing agent of a one-component system, a two-component system or the like may be used in embodiments as developing device 4. There is no particular limitation on toners that may be used in embodiments.

Contact-type transfer-charging devices using a belt, a roller, a film, a rubber blade or the like, or a scorotron-transfer charger or a corotron-transfer charger utilizing corona discharge may be employed as transfer device 5, in various embodiments.

Further, in embodiments, cleaning device 7 may be a device for removing a remaining toner adhered to the surface of photoreceptor 1 after a transfer step, and photoreceptor 1 repeatedly subjected to the above-mentioned image-formation process may be cleaned thereby. In embodiments, cleaning device 7 may be a cleaning blade, a cleaning brush, a cleaning roll or the like. Materials for the cleaning blade include urethane rubber, neoprene rubber and silicone rubber.

In the exemplary image-forming device shown in FIG. 2, the respective steps of charging, exposure, development, transfer and cleaning are conducted in turn in the rotation step of photoreceptor 1, thereby repeatedly performing image formation. Accordingly, even in embodiments in which the photoreceptor is used together with the contact-charging device or the cleaning blade, or further with spherical toner obtained by chemical polymerization, good image quality can be obtained without the occurrence of image defects such as fogging. That is, embodiments provide image-forming apparatuses that can stably provide good image quality for a long period of time.

Figure 3:
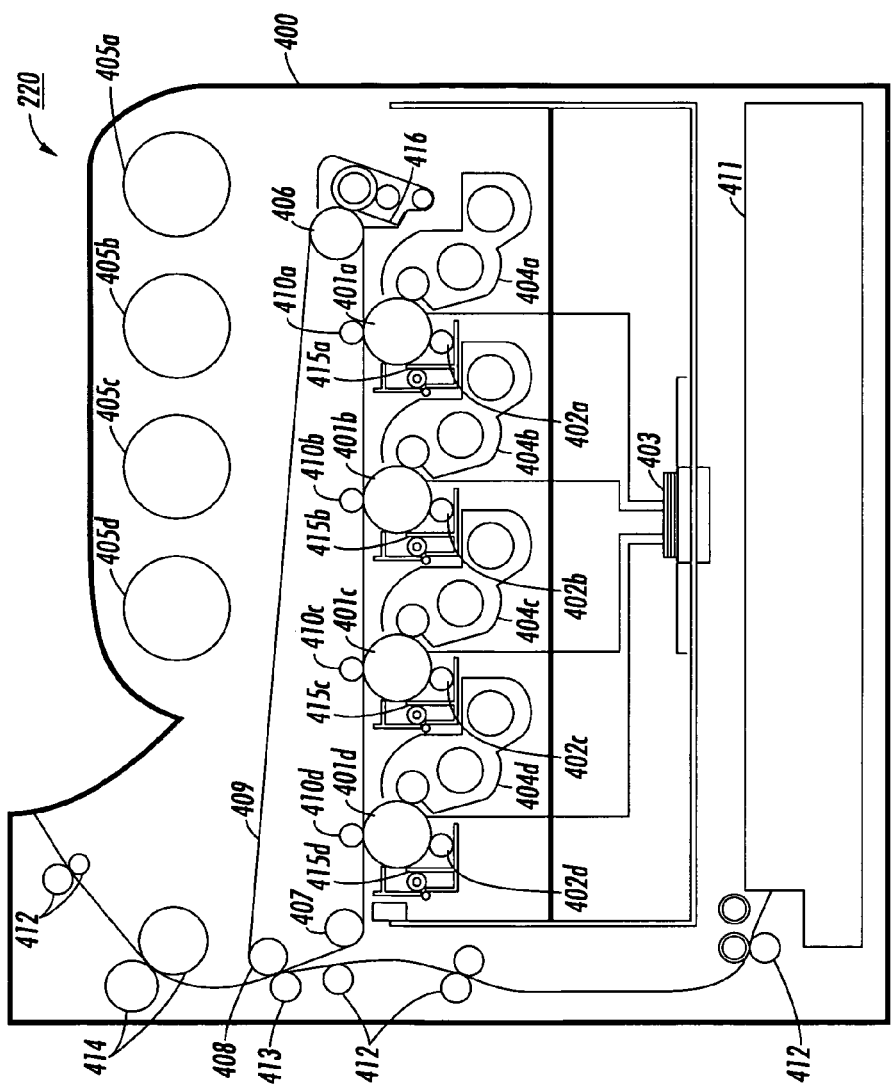
FIG. 3 is a schematic view showing another embodiment of an image-forming apparatus.

FIG. 3 is a cross sectional view showing another exemplary embodiment of an image-forming apparatus. Image-forming apparatus 220 shown in FIG. 3 is an image-forming apparatus of an intermediate-transfer system, and four photoreceptors 401a to 401d are arranged in parallel with each other along intermediate-transfer belt 409 in housing 400.

Here, photoreceptors 401a to 401d carried by image-forming apparatus 220 are each the photoreceptors of embodiments. Each of photoreceptors 401a to 401d may rotate in a predetermined direction (counterclockwise on the sheet of FIG. 3), and charging rolls 402a to 402d, developing device 404a to 404d, primary transfer rolls 410a to 410d and cleaning blades 415a to 415d are each arranged along the rotational direction thereof. In each of the developing device 404a to 404d, four color toners of yellow (Y), magenta (M), cyan (C) and black (B) contained in toner cartridges 405a to 405d can be supplied, and primary transfer rolls 410a to 410d are each brought into abutting contact with photoreceptors 401a to 401d through intermediate-transfer belt 409.

Further, laser light source (exposure unit) 403 is arranged at a specified position in housing 400, and it is possible to irradiate surfaces of photoreceptors 401a to 401d after charging with laser light emitted from laser light source 403. This performs the respective steps of charging, exposure, development, primary transfer and cleaning in turn in the rotation step of photoreceptors 401a to 401d, and toner images of the respective colors are transferred onto intermediate-transfer belt 409, one over the other.

Intermediate-transfer belt 409 is supported with driving roll 406, backup roll 408 and tension roll 407 at a specified tension, and rotatable by the rotation of these rolls without the occurrence of deflection. Further, secondary transfer roll 413 is arranged so that it is brought into abutting contact with backup roll 408 through intermediate-transfer belt 409. Intermediate-transfer belt 409, which has passed between backup roll 408 and secondary transfer roll 413, is cleaned up by cleaning blade 416, and then repeatedly subjected to the subsequent image-formation process.

Further, tray 411, for providing a medium such as paper to which a toner image is to be transferred, is provided at a specified position in housing 400. The medium to which the toner image is to be transferred in tray 411 is conveyed in turn between intermediate-transfer belt 409 and secondary transfer roll 413, and further between two fixing rolls 414 brought into abutting contact with each other, with conveying roll 412, and then delivered out of housing 400.

According to exemplary image-forming apparatus 220 shown in FIG. 3, the use of photoreceptors of embodiments as photoreceptors 401a to 401d may achieve discharge-gas resistance, mechanical strength, scratch resistance, etc. on a sufficiently high level in the image-formation process of each of photoreceptors 401a to 401d. Accordingly, even when the photoreceptors are used together with contact-charging devices or cleaning blades, or further with spherical toners obtained by chemical polymerization, good image quality can be obtained without the occurrence of image defects such as fogging. Therefore, also according to the image-forming apparatus for color-image formation using the intermediate-transfer body, such as this embodiment, the image-forming apparatus which can stably provide good image quality for a long period of time is realized.

The above-mentioned embodiments should not be construed as limiting. For example, each apparatus shown in FIG. 2 or 3 may be equipped with a process cartridge comprising photoreceptor 1 (or photoreceptors 401a to 401d) and charging device 2 (or charging devices 402a to 402d). The use of such a process cartridge allows maintenance to be performed more simply and easily.

Further, in embodiments, when a charging device of the non-contact-charging system such as a corotron charger is used in place of contact-charging device 2 (or contact-charging devices 402a to 402d), sufficiently good image quality can be obtained.

Furthermore, in the embodiment of an apparatus that is shown in FIG. 2, a toner image formed on the surface of photoreceptor 1 is directly transferred to medium P to which the toner image is to be transferred. However, the image-forming apparatus of embodiments may be further provided with an intermediate-transfer body. This makes it possible to transfer the toner image from the intermediate-transfer body to medium P to which the toner image is to be transferred, after the toner image on the surface of photoreceptor 1 has been transferred to the intermediate-transfer body. As such an intermediate-transfer body, there can be used one having a structure in which an elastic layer containing a rubber, an elastomer, a resin or the like and at least one covering layer are laminated on a conductive support.

In addition, the image-forming apparatus of embodiments may be further equipped with a static eliminator such as an erase light irradiation device. This may prevent incorporation of residual potential into subsequent cycles when the electrophotographic photoreceptor is used repeatedly. Accordingly, image quality can be more improved.

EXAMPLES

The embodiments as discussed above are illustrated in greater detail with reference to the following Examples and Comparative Examples, but the invention should not be construed as being limited thereto. In the following examples and comparative examples, all the "parts" are given by weight unless otherwise indicated.

Example 1

Into a 5 L flask, fitted with mechanical stirring, argon inlet, sodium hydroxide scrubber and 18-inch dry ice/isopropanol condenser, were placed 100 grams of methyldichlorosilane (molecular weight: 115.04), 50.9 grams of divinylbenzene (technical grade 50%, molecular weight: 130.19) and 200 mL toluene. To this mixture, 20 drops of the Karstedt catalyst (available from Aldrich Chemical Company) were added. After an induction period of more than 15 minutes, a rapid exothermic reaction is observed. The reaction is stirred overnight (for more than 10 hours) to ensure complete reaction.

Upon completion of the reaction, 1.5 L of THF was added. Then, a mixture of 100 grams of methanol and 215 grams of triethylamine was added dropwise. The mixture was stirred for 2 hours after complete addition. The mixture was filtered to remove insoluble salts, and excess methyldimethoxysilane (boiling point: 61° C.) and solvent were removed. The residue was distilled under reduced pressure. The low-boiling fractions were confirmed to be aromatic hydrocarbons by a combination of gas chromatography and $^1$H NMR. The high-boiling fraction was a mixture of aromatic-silane compounds, such as those shown below and similar Markovnikov and anti-Markovnikov addition products. Yield was 105 grams of aromatic silane compounds.

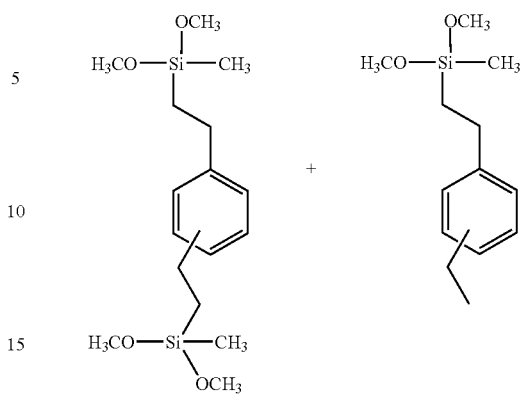

The aromatic-silane compound mixtures of Example 1 were characterized by GC and $^1$H NMR. The reaction produces a mixture of ten different compounds, representing both Markovnikov (M) and anti-Markovnikov (A) addition to m-divinylbenzene, p-divinylbenzene and ethylvinylbenzene.

Example 2

For Example 2, siloxane-layer coating formulations was prepared as follows:

Into a 5 L flask, fitted with mechanical stirring, argon inlet, sodium hydroxide scrubber and 18-inch dry ice/isopropanol condenser, an arylamine compound of formula (33), the material of Example 1, methanol and an ion-exchange resin, AMBERLYST 15 (available from Rohm & Haas Co. Corp.) were combined in the amounts indicated in Table 2. The reaction mixture was stirred for three hours.

After three hours, n-butanol and water were added in the amounts indicated in Table 2. The reaction mixture was allowed to polymerize for 30 minutes.

Following polymerization, the reaction mixture was stabilized by the addition of aluminum trisacetylacethonate (Al(AcAc)$_3$), acetyl acetone (AcAc), a polyvinyl butyral of formula (34) and 2,6-di-tert-butyl-4-methylphenol (BHT), in the amounts indicated in Table 2.

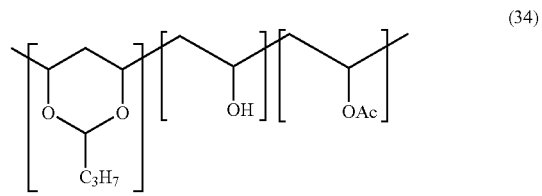

(34)

Comparative Example 1

For Comparative Example 1, a siloxane-containing layer coating formulation was prepared as in Example 2, using the compositional amounts set forth in Table 2, including a compound of formula (35).

TABLE 2

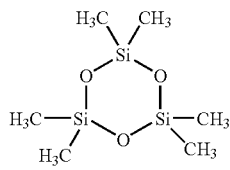

(35)

| Material | Comparative Example 1 (g) | Example 2 (g) |
| --- | --- | --- |
| Arylamine compound of formula (33) | 5.5 | 5.5 |
| Compound of III-3 | 3 | — |
| Example 1 | — | 3 |
| Compound of formula(35) | 0.5 | — |
| MeOH | 5.5 | 5.5 |
| AMBERLYST 15 | 0.55 | 0.55 |
| n-BuOH | 16 | 16 |
| $H_2O$ (2 equivalents) | 2.46 | 2.46 |
| $Al(AcAc)_3$ | 0.09 | 0.09 |
| AcAc | 0.09 | 0.09 |
| polyvinyl butyral of formula (34) | 1 | 1 |
| BHT | 0.09 | 0.09 |

The resulting formulations of Example 2 and Comparative Example 1 are summarized in Table 3.

TABLE 3

| | Comparative Example 1 | Example 2 |
| --- | --- | --- |
| Total (grams) | 34.23 | 33.73 |
| Solid Content (grams) | 10.27 | 9.77 |
| Concentration (%) | 30.00 | 28.97 |

It may be noted that phase separation after the addition of the polymeric binder indicates that the binder is incompatible with the siloxane-containing matrix, which may be due to higher degrees of polymerization.

Example 3

The formulation of Example 2 was coated onto two photoreceptors A and B for evaluation. As shown in Table 4, the thickness and quality of the coatings were good.

TABLE 4

| 30 mm drum | Example 3A | Example 3B |
| --- | --- | --- |
| Full thickness (μm) | 28.3 ± 0.2 | 28.7 ± 0.3 |
| Charge transport layer thickness (μm) | 20.3 ± 0.3 | 20.3 ± 0.3 |
| Overcoat layer thickness (μm) | 3.8 ± 0.2 | 4.2 ± 0.3 |
| Coating Quality | Good | Good |

Figure 5:
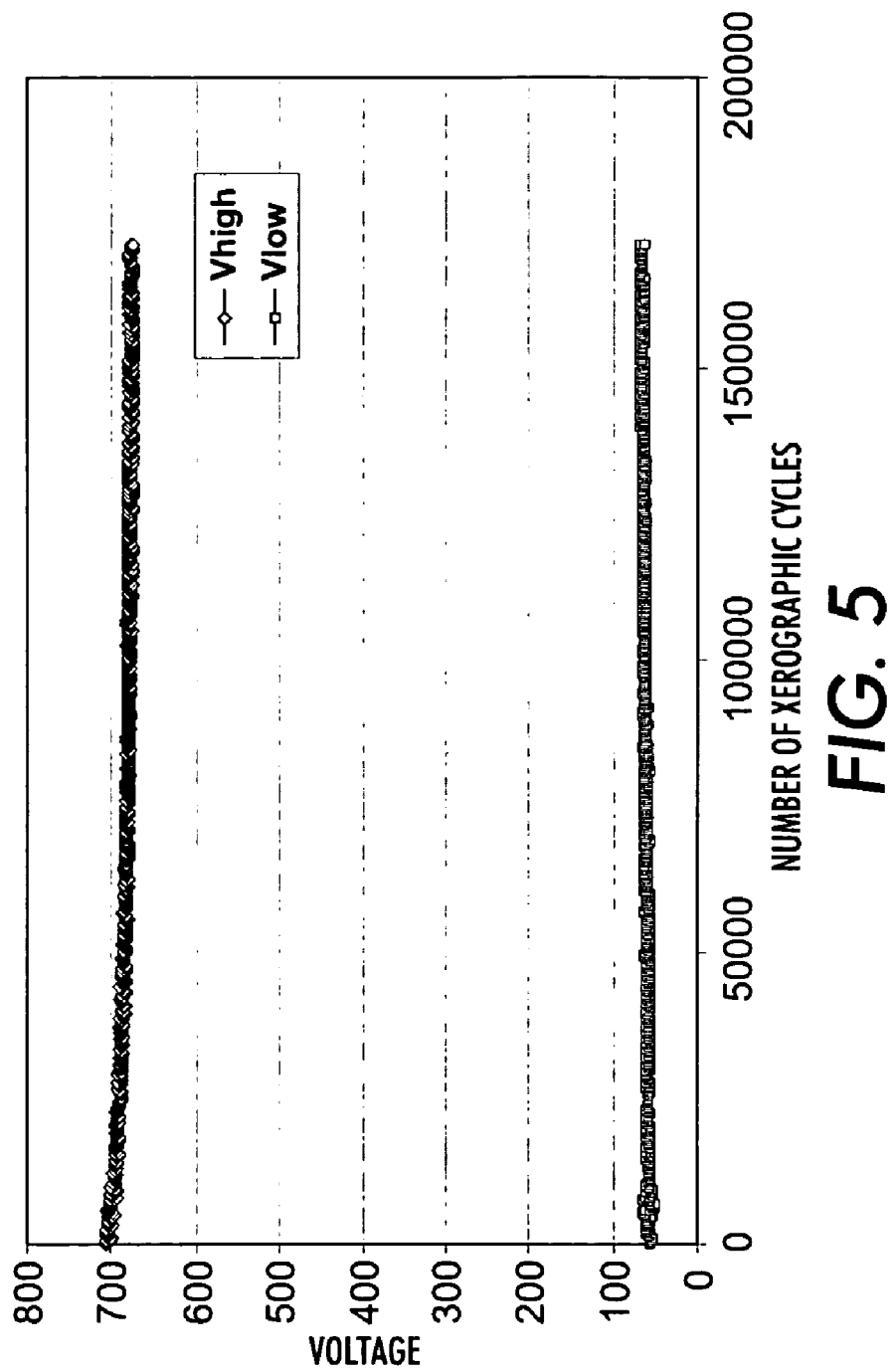
FIG. 5 is a graphical representation of the electrical performance of photoreceptors of an exemplary embodiment.

The photoreceptors of Example 3A and 3B did not demonstrate any electrical issues when subjected to long-term cycling under hypermode electrical cycling conditions, as shown in FIG. 4. As shown in FIG. 5, the photoreceptors of Example 3A and 3B showed lower starting torque, compared to conventional photoreceptors that include a siloxane-containing compound, and showed a comparable running torque (without toner), compared to conventional photoreceptors that include a siloxane-containing compound.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A process for preparing an aromatic matrix material comprising:
   reacting an aromatic compound selected from the group consisting of vinylbenzenes, alkylvinylbenzenes, divinylbenzenes, and mixtures thereof, and a silating agent in the presence of a metal hydrosilylation catalyst to produce a silyated compound; and
   further reacting the silylated compound with an alcohol.

2. The process according to claim 1 wherein the aromatic compound is chosen from the group consisting of ethylvinylbenzenes, divinylbenzenes, and mixtures thereof.

3. The process according to claim 1, wherein the aromatic compound comprises more than 10 weight % of the divinylbenzenes.

4. The process according to claim 1, wherein the silating agent is chosen from the group consisting of $C_1$-$C_5$ alkyldihalosilanes, and mixtures thereof.

5. The process according to claim 1, wherein the silating agent is methyldichlorosilane.

6. The process according to claim 1, wherein the metal hydrosilylation catalyst is chosen from the group consisting of platinum hydrosilylation catalysts, and mixtures thereof.

7. The process according to claim 6, wherein the platinum hydrosilylation catalyst is $Pt_2$(divinyltetramethyldisiloxane)$_3$.

8. The process according to claim 1, wherein the alcohol is chosen from the group consisting of $C_1$-$C_5$ alcohols, and mixtures thereof.

9. The process according to claim 8, wherein the alcohol is methanol.

10. The process according to claim 1, wherein reacting the silylated compound is conducted in the presence of an amine.

11. The process according to claim 10, wherein the amine is chosen from the group consisting of tertiary amines and mixtures thereof.

12. The process according to claim 11, wherein the amine is triethylamine.

* * * * *